United States Patent [19]
Chen et al.

[11] Patent Number: 5,854,011
[45] Date of Patent: Dec. 29, 1998

[54] METHOD AND COMPONENTS FOR THE DETECTION OF YEASTS AND/OR MOLDS IN A SAMPLE

[75] Inventors: Chun-Ming Chen, Falmouth; Haoyi Gu, Portland, both of Me.

[73] Assignee: Idexx Laboratories Incorporated, Westbrook, Me.

[21] Appl. No.: 769,512

[22] Filed: Dec. 19, 1996

[51] Int. Cl.$^6$ ............... C12Q 1/37; C12Q 1/24; C12N 9/99; C12N 9/50
[52] U.S. Cl. ............... 435/24; 435/30; 435/219; 435/184
[58] Field of Search ............... 435/34, 24, 30, 435/31, 32, 231, 184, 195, 212, 219

[56] References Cited

U.S. PATENT DOCUMENTS

| | | | |
|---|---|---|---|
| 4,140,580 | 2/1979 | Gibson et al. | 435/34 |
| 4,314,936 | 2/1982 | Yaron et al. | 530/331 |
| 4,591,554 | 5/1986 | Komura et al. | 435/18 |
| 4,636,492 | 1/1987 | Kettner et al. | 514/18 |
| 4,675,289 | 6/1987 | Kanou et al. | 435/18 |
| 4,874,695 | 10/1989 | Pincus | 435/19 |
| 5,073,488 | 12/1991 | Matner et al. | 435/31 |
| 5,236,827 | 8/1993 | Sussman et al. | 435/34 |
| 5,429,933 | 7/1995 | Edberg | 435/34 |

FOREIGN PATENT DOCUMENTS

| | | |
|---|---|---|
| 01 95212 | 10/1986 | European Pat. Off. . |
| 91 14787 | 10/1991 | WIPO . |
| 96 49080 | 12/1996 | WIPO . |

OTHER PUBLICATIONS

Fittkau et al. "Bovine eye lens leucine aminopeptidase. Kinetic studies with substrates and substrate–like inhibitors", Intracell. Protein Catabolism, Proc. symp. (1973) 6:480–4. (abstract), 1973.

Christ, Arthur E. Jr, "Comparison of the Murex *C. albicans*, Albicans–Sure, and BactiCard Candida Test Kits with the Germ Tube Test for Presumptive Identification of *Candida albicans*," *J. Clinical Microbiology* 34:2616–2618 (1996).

Bobey and Ederer, "Rapid Detection of Yeast Enzymes by Using 4–Methylubelliferyl Substrates," *J. Clinical Microbiology* 13:393–394 (1981).

Deak and Beuchat in *Handbook of Food Spoilage Yeasts*, CRC Press, Boca Raton, pp. 3–5, vol. 11, No. 124–125 (1996).

Jay, *Modern Food Microbiology*, 4th edition, Chapman & Hall, New York, pp. 26–35 (1992).

Perry and Miller, "Umbelliferyl–Labeled Galactosaminide as an Aid in Identification of *Candida albicans*," *J. Clinical Microbiology* 25:2424–2425 (1987).

Peeler et al., "Ch. 6—The Most Probable Number Technique," pp. 105–120 and Ch. 16—Yeasts and Molds, pp. 239–248 in *Compendium of Methods for the Microbiological Examination of Foods*, edited by Vanderzant and Splittstoesser, American Public Health Association (1992).

*Primary Examiner*—Jean C. Witz
*Assistant Examiner*—Susan Hanley
*Attorney, Agent, or Firm*—Lyon & Lyon LLP

[57] ABSTRACT

A composition and method for detecting the presence or amount of yeasts and molds in a test sample is presented. The composition contains a substrate and an inhibitor for an aminopeptidase. The substrate has a signal moiety capable of providing a detectable signal when cleaved by an aminopeptidase in yeasts or molds. The aminopeptidase inhibitor serves to reduce the endogenous aminopeptidase activity in the test sample. The method to detect yeasts or molds in a sample includes inoculating a test sample with the disclosed composition, incubating the sample and observing any detectable signal that indicates the presence of yeasts or molds.

22 Claims, No Drawings

METHOD AND COMPONENTS FOR THE DETECTION OF YEASTS AND/OR MOLDS IN A SAMPLE

FIELD OF THE INVENTION

This invention relates to the fields of chemistry, biology and microbiology. In particular, it relates to a method and a medium for detecting the presence of yeasts and molds in a sample by means of aminopeptidase activity.

BACKGROUND OF THE INVENTION

Yeasts and molds are eukaryotic microorganisms; they are ubiquitous in natural environments, namely, soil, air, water, and plant surfaces. Because of their heterotrophic nature and their ability to adapt to a wide range of environmental conditions, these microbes are frequently encountered as an expensive nuisance in and on various commodities including food ingredients, processed foods, beverages, inadequately cleaned food processing equipment, and food storage facilities. In addition, some yeasts and molds possess potential hazard to human and animal health. For example, numerous molds produce mycotoxins and some yeasts and molds are responsible for human and animal infections.

Yeast or mold contamination in food and other commodities can result in substantial economic losses for the producer, the processor, and the consumer. Rapid and accurate determinations of yeast and/or mold contamination in a commodity (such as, food ingredients, processed foods, and beverages), are important for the production of high-quality food products in the food industry.

Current practices for routine determination of yeasts and molds in a food commodity rely largely on conventional culturing techniques for enumerating viable fungal cells on solid agar media. Examples include acidified potato agar media, antibiotic supplemented potato dextrose agar media, and to a less extent Petrifilm YM® system (See generally, *Compendium of Methods for the Microbiological Examination of Foods*, 1992. Third Edition, Edited by Carl Vanderzant and Don F. Splittstoesser, Complied by the APHA Technical Committee on Microbiological Methods for Foods, and Bacteriological Analytical Manual, Food and Drug Administration, 1992. Published and Distributed by AOAC International).

These methods, although widely accepted, have a number of disadvantages in that they are, in general, labor intensive and give low reproducibility. In addition, a common problem encountered in the traditional methods is that the predominate mycelial growth of certain molds often prevents accurate enumeration of the viable cells. Most importantly, these methods require a 5 day incubation period at 25° C. before accurate results can be obtained. The long incubation period of these methods can require that food products be stored for several days, until the presence or concentration of contaminating yeasts and/or molds is finally known. Thus, there is a need for improved tests and related materials. If the test procedures could be simplified, and test results obtained in a shorter period of time, it would allow manufacturers to release products saving storage costs without scarifying product quality and integrity. This would represent significant labor and cost savings for manufacturers and significant corresponding benefits for the consumer.

There have been attempts to measure yeasts and molds in a sample other than by conventional plating techniques. These methods include:

(1) electrometric techniques (i.e. impedance, capacitance, and conductance) which measure changes in electrical resistance of the medium due to metabolic breakdown of substrates by target microbes, (2) quantification of carbon dioxide, (3) ATP bioluminescence assays, (4) antibody-based assays, (5) direct microscopic analysis using fluorescent or selective dyes, (6) indicators of microbial growth have also been used to monitor the growth of target microbes which change color only after the growth of yeasts and molds is detected.

Microbial growth indicators normally react chemically with a metabolic by-product produced by target microbes resulting in a color change in the medium. Examples of chemicals which change color in the presence of pH changes associated with microbial growth include aniline blue, phenol red, bromocresol blue, and neutral red. For example, Gibson, U.S. Pat. No. 4,140,580 uses aniline blue, a chemical which changes color in the presence of acidic metabolic waste products produced by yeasts.

Enzymatic catalysis for hydrolyzing chromogenic or fluorogenic substrates to yield a detectable signal has been used in a number of microbial diagnostic applications.

Townsend and Chen, describe a method and composition for detecting bacterial contamination in food products in U.S. application Ser. No. 08/484,593, filed Jun. 7, 1995, which is incorporated by reference herein. The method of Townsend and Chen comprises use of a number of fluorogenic enzyme substrates in a growth medium. This growth medium detects bacterial contamination in a sample by detecting bacterial enzymes (e.g. phosphatase, β-glucosidase, and L-alanine aminopeptidase)from diverse microbial species. The liberated fluorescent moieties exhibit detectable signals with an identical emission wavelength. This procedure takes advantage of combining different bacterial enzyme activities from diverse microbes, to create a broader enzyme activity spectrum; the broadened spectrum enables the detection of total bacteria in a test sample.

Koumura et. al., in U.S. Pat. No. 4,591,554 describes the use of 4-methylumbelliferyl derivatives fluorogenic analysis to detect and determine the number of microorganisms based on the amount of liberated umbelliferone derivatives. According to the method, microorganisms at more than $10^4$ cfu/ml can be determined by contacting a sample solution with the umbelliferone derivatives, and measuring the amount of fluorescent umbelliferone derivatives liberated. In the Koumura patent, cell lysis is required to increase the amount of liberated enzymes. In other cases, pH adjustment of the mixture and centrifugation of the mixture to remove insoluble cells are required at the end of incubation.

Perry and Miller used an umbelliferyl-conjugated N-acetyl-β-D-galactosaminide for specific identification of a pathogenic yeast, Candida albicans, (*J. Clin. Microbiol.* 25:2424–2425 (1987)).

Enzymes in yeasts and molds have been identified which can hydrolyze chromogenic or fluorogenic substrates under appropriate conditions to produce a colored or fluorescent signal that can be detected either visually or spectrophotometrically. These enzymes, including: phosphatase, esterase, α-glucosidase, β-glucosidase, N-acetyl-β-D-galactosaminidase, urease, and proteases, have been identified to be present in one or more yeasts and molds. Most of these enzymes, however, are specific to a particular species or are only specific to certain species of yeasts and molds. For example, N-acetyl-β-D-galactosaminidase is unique to the pathogenic yeast, *Candida albicans*. Phosphatase activity is not universally present in all yeast and mold; only about 50–60% of the yeasts and molds possess this enzyme. In order to detect the majority (at least 95%) or all yeasts and molds species in a test sample, one or more ubiquitous yeast and mold enzymes which can hydrolyze the substrates and produce a detectable signal must be identified and used as an indication of the presence of these organisms. One enzyme, esterase, that is widely present in yeasts and molds hydrolyzes chromogenic or fluorogenic ester substrates to produce a detectable signal. These ester substrates, however, are poorly soluble in an aqueous phase and often require acidic conditions to maintain their stability.

SUMMARY OF THE INVENTION

Prior to the present invention, aminopeptidases were not known to be ubiquitous enzymes in yeasts and molds. The present invention comprises that the concentration of yeasts and molds in a test sample is measured as a function of aminopeptidase activity acting on the respective enzyme substrates in the medium. Accordingly, a medium is provided which contains one or more aminopeptidase substrates; these substrates have a nutrient moiety and a detectable moiety linked together by a covalent peptide bond. When the substrate is hydrolyzed by aminopeptidase to create a separate detectable moiety, it causes or produces a detectable signal. Thus, these substrates produce detectable signals when any one of the aminopeptidases is present in the medium. An aminopeptidase specific inhibitor can be included in the medium to prevent signal interference due to the endogenous aminopeptidase activity in the biological matrix. The aminopeptidase inhibitor is preferably used in such an amount it that only inhibits the endogenous enzyme activity without affecting the detection of yeasts and molds; this step can be performed as disclosed herein by methods such as serial dilution, as appreciated by one of ordinary skill in the art.

Accordingly, a medium is disclosed for detecting yeasts and molds in a biological sample. In certain preferred embodiments, the medium provides effective results by employing a newly identified ubiquitous enzyme in yeasts and molds: aminopeptidase. The medium is preferably provided in combination with an inhibitor for the aminopeptidase enzyme. The inhibitor is provided at a level that reduces endogenous activity in test samples, but which does not impair the activity in yeasts or molds. In addition, buffer ingredients, carbohydrates, amino acids, trace elements, salts, and growth stimulators provided in the medium allow sufficient growth of the organism, so that the detectable signal in the sample due to hydrolysis of aminopeptidase substrates is more effectively observed. A presently preferred composition for detecting yeasts and molds is described in Table IV.

Definitions:

By "aminopeptidase" is meant an enzyme whose enzymatic activity is capable of hydrolyzing a covalently linked peptide bond of an enzyme substrate or a plurality of enzyme substrates. In a preferred embodiment of this invention, the enzymatic activity of one or more aminopeptidases is used to detect or measure the concentration of yeasts and molds in a sample. In one preferred embodiment, the aminopeptidase enzyme is leucine aminopeptidase and/or alanine aminopeptidase; as disclosed herein, these two enzymes have recently been found to be ubiquitous in yeasts and molds.

By "enzyme substrate" is meant a molecule on which an enzyme acts. The enzymatic reaction usually involves hydrolyzing one or more covalent bonds. The substrates typically consist of covalently linked nutrient and detectable moieties. Upon being hydrolyzed by a microbial enzyme, the substrate liberates a separate detectable moiety in the medium. In preferred embodiments, the enzyme substrates are selected from the group of aminopeptidase substrates that are listed in Table III. This list is not meant to exclude aminopeptidase substrates which have yet to be discovered, substrates which may later be identified and included in this list by those of ordinary skill in the art. In alternative preferred embodiments, the enzyme substrate is L-leucine-7-amido-4-methylcoumarin or L-alanine-7-amido-4-methylcoumarin, or both in combination.

By "biological matrix" is meant an environment or milieu in which microbial growth is occurring or may occur.

By "nutrient moiety" is meant a molecule or substance which is a nutrient or metabolic source for yeasts and molds, including but are not limited to: amino acids (e.g. alanine, leucine, arginine, valine, etc.), carbon sources (e.g. glucose, galactose, fructose, etc.), minerals (e.g. sulfate, phosphate, etc.). In one preferred embodiment of the invention, the nutrient moieties of the enzyme substrates are amino acids.

By "detectable moiety" is meant a molecule or substance which can be affiliated with a nutrient moiety or exist as a discrete entity. The detectable moiety does not cause or produce a detectable signal when it is affiliated with (e.g., covalently bonded to) a nutrient moiety. However, when an enzyme from a viable yeast or mold hydrolyzes the substrate, a detectable moiety is released and causes or is capable of producing a detectable signal. In preferred embodiments, the detectable moieties are chromogens which preferably produce a color change observable in the visible wavelength range (alternatively in the ultraviolet or infrared spectra), or fluorogens which emit fluorescence when properly excited by an external energy source.

Examples of detectable moieties include, but are not limited to: ortho-nitrophenyl, 4-methylumbelliferone, para-nitroanilide, 4-methoxy-β-naphthylamide, 7-amido-4-methylcoumarin.

By "detectable signal" is meant a characteristic change in a medium or sample that is observable or measurable by physical, chemical, or biological means known to those skilled in the art. Such a detectable signal may be assayed by visual, tactile, or olfactory means. For example, a change in emission or absorbance of visible or invisible light or radio waves at a certain wavelength, electrical conductivity, emission of gas, or odor is detected. A detectable signal may also be a change in physical state such as between solid, liquid and gas. Typically, a detectable signal is measured visually; in preferred embodiments, detectable signals comprise a change in color or fluorescent emission of the medium.

By "identical type of detectable signal" is meant that the separate detectable moieties hydrolyzed from different enzyme substrates cause or produce detectable signals that are measurable by the same or substantially the same physical, chemical or biological parameter, including, but are not limited to, color, fluorescent emission, odor, or electric conductivity. The intensity or quantity of signals caused or produced by different separate detectable moieties may be different for detectable moieties from different substrates. For example, yellow colors of different intensity would be considered of the identical type. Fluorescence with the same emission wavelength but of different intensity would be considered of the identical type. For example, a visible color change and fluorescence would not be considered to be identical types of detectable signals.

By "endogenous enzyme activity" is meant an enzyme that is present in a biological matrix from which a yeast and mold concentration is sought to be determined. Endogenous enzymes that act on substrates of the invention can hydrolyze those substrates and cause signal interference in the medium. Presence of such interference can impair accurate determination of yeast and mold presence or concentration in the test sample.

By "food product" is meant any substance or composition which is consumed by a human or animal for nourishment, or sustenance or metabolism. A food product can comprise, but is not limited to: meat, dairy, fruit, vegetable, grain, cereal, alcohol, water and beverage products. For example, a food product can be flour, packaged meat products or beverages.

By "enzyme inhibitor" is meant a molecule or a substance whose presence prevents or inhibits enzyme catalysis of the enzyme substrate for that enzyme. Preferably, enzyme inhibitors are included in the medium to prevent or reduce endogenous aminopeptidase activity in biological matrices. Alternatively, the inhibitors are added to the sample before sample is added to the medium, or the inhibitors are added directly to the biological matrix.

By "test sample" is meant a component taken from a food product, a human or animal test subject, pharmaceutical or cosmetic commodity, soil, water, air or other environmental source, or any other source from which a yeast and mold concentration is to be determined. A test sample may be taken from a source using techniques known to one skilled in the art, including are not limited to, those described or referred to in *Compendium of Methods for the Microbiological Examination of Foods*, Third Edition, Edited by Carl Vanderzant and Don F. Splittstoesser, Compiled by the APHA Technical Committee on Microbiological Methods for Foods, incorporated by reference herein.

By "yeast" is meant a typically unicellular fungus that reproduces asexually. Yeast includes one or more species of the following organisms existing or co-existing collectively in a test sample. For example, yeasts include those listed in Table I and described in: Tibor Deak and Larry Beuchat, *Handbook of Food Spoilage Yeasts*, pp. 3–11, 124–25 (1996) and James, M. Jay, *Modern Food Microbiology*, 4th Ed., pp. 26–35 (1992) each of which are incorporated by reference herein. The term "yeasts" also refers to the array of yeasts found, e.g., in a test sample. The term is not limited to mean any given number of these species and is not meant to exclude species which have yet to be discovered but may later be identified and included in this definition by those of skill in the art.

TABLE I

Common Foodborne Yeast Genera & 60 Common Yeast Strains (93% Combined Frequency in Foods)

| Genera | Top 60 Foodborne Yeast Strains | |
|---|---|---|
| Candida | Candida boidinii | Kluyveromyces marxaanus |
| Cryptococcus | Candida apicola | Metschnikowia pulcherrima |
| Debaryomyces | Candida albicans | Pichia angusta |
| Galactomyces | Candida zeylanoides | Pichia subpelliculosa |
| Hanseniaspora | Candida vini | Pichia mambranaefaciens |
| Issatchenkia | Candida versatilia | Pichia jadinii |
| Kluyveromyces | Candida tropicalis | Pichia guilliermondii |
| Metschnikowia | Candida stellata | Pichia fermentans |
| Pichia | Candida sake | Pichia farinosa |
| Rhodotorula | Candida rugosa | Pichia burtonii |
| Saccharomyces | Candida parapsilosis | Pichia anomala |
| Saccharo- | Candida norvergica | Rhodotorula glutinis |
| mycodes | Candida magnoliae | Rhodotorula mucilaginosa |
| Schizosaccha- | Candida intermedia | Rhodotorula minuta |

TABLE I-continued

Common Foodborne Yeast Genera & 60 Common Yeast Strains (93% Combined Frequency in Foods)

| Genera | Top 60 Foodborne Yeast Strains | |
|---|---|---|
| romyces | Candida incospicua | Saccharomyces bayanus |
| Sporobolmyces | Candida glabrata | Saccharomyces kluyveri |
| Torulaspora | Candida etchellsii | Saccharomyces exiguus |
| Trichosporon | Candida catenulata | Saccharomyces cerevisiae |
| Yarrowia | Cryptococcus albidus | Saccharomycodes ludwigii |
| lipolytica | Cryptococcus laurentii | Saccharomycopsis fibuligera |
| Zygosacchromyces | Cryptococcus humicolus | Saccharomycopsis pombe |
| | Debaryomyces etchellsii | Sporobolmyces roseus |
| | Debaryomyces polymorphus | Torulaspora delbrueckii |
| | Debaryomyces hansenii | Trichosporon moniliforme |
| | Galactomyces geotrichum | Trichosporon pullulans |
| | Haneniaspora guilliermonii | Yarrowia lipolytica |
| | Haneniaspora uvarum | Zygosacchromyces bailii |
| | Issatchenkia orientalis | Zygosacchromyces rouxii |
| | Kluyveromyces lactis | Zygosacchromyces microellipsoides |
| | Kluyveromyces thermotolerans | Zygosacchromyces bisporus |

By "mold" is meant a fungus. For example, mold includes one or more species of the following microorganisms existing or co-existing collectively in a test sample: Aspergillus, Penicillin etc. This term is not limited to mean any given number of these species and is not meant to exclude species which have yet to be discovered but may later be identified and included in this genus by those skill in the art. The molds include those listed in Table II and described or referred to *Modern Food Microbiology*, 4th Ed., supra.

TABLE II

Common Foodborne Mold Genera

| Genera | Important Foodborne Mold Strains | |
|---|---|---|
| Alternaria | Alternaria citri | Fusarium graminearum |
| Aspergillus | Alternaria alternata | Fusarium tricinctum |
| Botrytis | Alternaria solani | Geotrichum candidum |
| Byssochlamys | Alternaria tenuissima | Geotrichum albidum |
| Cladosporium | Aspergillus niger | Monilia sitophila |
| Colletotrichum | Aspergillus alliaceus | Mucor miehei |
| Fusarium | Aspergillus ostianus | Penicillium roqueforti |
| Geotrichum | Aspergillus mellus | Penicillium cyclopium |
| Monilia | Aspergillus clavatus | Penicillium patulum |
| Mucor | Aspergillus terreus | Penicillium expansum |
| Penicillium | Aspergillus soyae | Penicillium clavifome |
| Pullularia | Aspergillus glaucus | Penicillium viridicatum |
| Rhizopus | Aspergillus oryzae | Penicillium citrinum |
| Thamnidium | Aspergillus parasiticus | Pullularia pullulans |
| Trichothecium | Botrytis cinerea | Rhizopus stolonifer |
| | Byssochlamys fluva | Rhizopus oligosporus |
| | Byssochlamys nivea | Thamnidium elegans |
| | Cladosporium herbarum | Trichothecium roseum |
| | Cladosporium cladosporiodes | Colletotrichum gloeosporioides |

By the term "inoculation" is meant the time at which the test sample is mixed with medium of the invention.

The term "effective amount of nutrients" is an amount of nutrients within the range which allows or promotes growth and reproduction of a target microorganism. That is, an amount which allows target microbes or other organisms to adapt to the medium; continue metabolism; or, synthesize the necessary constituents for reproduction and to subsequently reproduce.

The term "effective amount of enzyme inhibitors" means an amount of an enzyme inhibitor(s) within a range which reduces or prevents signal interference from endogenous enzyme activity in a biological matrix. That is, an amount of inhibitor which reduces or prevents endogenous enzyme interference without adversely affecting the ability of target microbes to adapt to the medium, to synthesize the necessary constituents for supporting metabolic activity and growth, or for reproduction. It is, however, not meant to identify only one embodiment and may vary depending upon such factors as sample size and concentration of microorganisms.

The terms "vitamins", "amino acids", "trace elements" and "salts" are meant to include all molecules, compounds, and substances classified in each category by those of skill in the art whether organic or inorganic. The combination of these categories is intended to include any substance which may be necessary for, or conducive to, maintaining life of microorganisms.

The term "target microbe" means the microorganism whose presence or absence is sought to be detected. For example, it includes any species of yeast or mold listed in Tables I and II.

The term "yeast and mold specific medium" means a medium which allows growth of yeasts and molds and allows for substantially less growth of any other component of a biological matrix. This term includes media which contain one or more antibiotics specific for inhibiting growth of heterotrophic bacteria but not yeasts and molds, and it includes media which alternatively or additionally contain one or more enzyme substrates which are preferably not hydrolyzed by enzymes from microorganisms other than the yeast or mold target microbe(s) to any substantial degree.

The term "substantial growth of yeasts and molds" means that the medium still allows specific (i.e., at least 90% accurate) and sensitive (i.e., at least 90% detection) assays of yeasts and molds, as measured relative to standard culture procedures.

DESCRIPTION OF THE PREFERRED EMBODIMENTS

For the first time in the art, yeasts and molds as a group have been identified to ubiquitously possess both L-leucine aminopeptidase and L-alanine aminopeptidase activity. As disclosed herein, substrates for these enzymes have appropriate solubility and stability in water, and can be effectively incorporated into a growth medium.

Enzymes that are ubiquitous in yeasts and molds could potentially be used to detect the presence of these microbes. Certain enzymes are known to be ubiquitous in yeasts and molds. However, the substrates for these ubiquitous enzymes are poorly soluble in an aqueous phase, and often require acidic conditions to maintain aqueous stability. The least water soluble enzyme substrates are generally the lipase or esterase substrates. Conversely, enzymes whose substrates are stable and soluble in the aqueous phase have not been known to be ubiquitous in yeasts and molds. Enzymes that are not ubiquitous are not well suited for use to detect total yeasts and molds.

Therefore, since these enzymes are universally present in yeasts and molds and their substrates have appropriate solubility and stability in water, these enzymes are preferably used as the target enzymes for detecting yeasts and molds in a sample. To achieve rapid results and yield an enhanced detectable signal, two or more fluorogenic substrates which can be metabolized by their corresponding enzymes are preferred. Most preferably, the multiple enzymes contain the same detectable moiety. In addition, medium composition need to be adjusted to support the maximum growth and expression of target enzyme activities from diverse yeasts and molds.

When viable yeasts or molds are present in a test sample, either a substrate of L-leucine aminopeptidase or L-alanine aminopeptidase can be metabolized to liberate a detectable moiety in the medium. To achieve rapid results and yield an enhanced detectable signal, an embodiment of the growth medium can comprise two or more aminopeptidase substrates which comprise detectable moieties. The enzyme substrates are metabolizable by their corresponding enzymes. Particularly preferred, is a medium comprising two or more aminopeptidase substrates that contain the same type of, or the same detectable moiety.

The present invention relates to a method and medium for measuring yeast and/or mold concentrations in a test sample. One of the challenges in designing an enzyme-based microbial diagnostic test is to select one or more appropriate enzymes whose presence concomitantly reveals the presence of target microbes.

Another problem often encountered in designing an enzyme-based microbial detection system is signal interference due to substrate hydrolysis by endogenous enzymes in the biological matrices. Thus, one design challenge is to prevent or reduce signal interference from the endogenous enzyme activity in biological matrices. This challenge is not easily met since various food matrices may contain different levels of endogenous enzyme activity. If a biological matrix contains high levels of background enzymatic activity but low levels of yeast or mold contamination; the level of endogenous activity cannot be overcome by serial dilution.

To overcome this problem, the present invention can comprise a protease inhibitor at a concentration that suppresses or reduces endogenous aminopeptidase activities in biological matrices, without affecting the microbial aminopeptidase activities.

For example, endogenous aminopeptidase activity has been overcome in the following food matrices by the use of a protease inhibitor while still permitting an effective assay result: peanut butter, wheat, corn meal, wheat flour, sweetened concentrated milk, corn, baby peas, black pepper, paprika, cottage cheese, raspberry yogurt, and ground beef. For each of these substances the background aminopeptidase activity was significantly inhibited or reduced to an extent so as not to interfere with the result interpretation.

It is to be noted that the invention can also comprise use of serial dilution together with a protease inhibitor; such a combination has been used to overcome the background aminopeptidase activity in bleached flour. A combination of serial dilution and use of a protease inhibitor is preferred for those food matrices in which yeasts or molds are normally present in high concentration. These embodiments minimize or prevent signal interference due to the hydrolysis of enzyme substrates by endogenous aminopeptidase activity.

Thus, in a first aspect, this invention features a medium for detecting one or more enzymes in yeasts and molds; in a preferred embodiment the enzyme is an aminopeptidase. According to the present invention, a medium is provided, as is a related method for measuring the concentration of yeasts and molds as a function of microbial aminopeptidase activities. The presence of at least one of these enzymes in any given yeast and mold species is detected by the appearance of a detectable signal, such as a fluorescent signal or a visibly colored signal.

In a preferred embodiment, one or more enzyme substrates are included in the growth medium specific for yeasts and molds. Each enzyme substrate is hydrolyzed by a different microbial aminopeptidase to cause or produce a detectable signal. In preferred embodiments, each signal has an essentially identical emission spectrum. In preferred embodiments, the medium contains an effective amount of biological buffers, carbohydrates, vitamins, amino acids, elements, salts ingredients, growth stimulators, and selective agents to provide for viability and specific enrichment of yeasts and molds in the presence of the aminopeptidase substrates.

In preferred embodiments, microbial aminopeptidases include, but are not limited to, leucine aminopeptidase and alanine aminopeptidase. In preferred embodiments, the peptidase substrates are selected from the group of aminopeptidase fluorogenic substrates that are listed in Table III. In addition, the presently preferred aminopeptidase substrates are set forth in Table IV. It is to be understood that this list does not exclude other known chromogenic aminopeptidase substrates, and aminopeptidase substrates which have yet to be discovered but later identified and included in this list by those of ordinary skill in the art.

Table III.
AMC (7-Amido-4-methylcoumarin) Aminopeptidase Substrates
N-o-Acetyl-lysine-7-amido-4-methylcoumarin acetate
N-Acetyl-L-phenylalanyl-L-arginine-7-amido-4-methylcoumarin hydrochloride
L-Alanine-7-amido-4-methylcoumarin
β-Alanine-7-amido-4-methylcoumarin TFA
D-Alanine-7-amido-4-methylcoumarin TFA
L-Alanine-7-amido-4-methylcoumarin TFA
L-Alanine-7-amido-4-methylcoumarin TFA
L-Alanine-7-amido-4-trifluoro-methylcoumarin TFA
L-Alanyl-L-alanyl-L-phenylalanine-7-amido-4-methylcoumarin
L-Alanyl-L-alanyl-L-phenylalanine-7-amido-4-methylcoumarin TFA
D-Alanyl-L-leucyl-L-lysine-7-amido-4-methylcoumarin Salt
L-Arginine-7-amido-4-methylcoumarin hydrochloride
L-Arginyl-L-arginine-7-amido-4-methylcoumarin trihydrochloride
L-Asparagine-7-amido-4-methylcoumarin TFA
L-Aspartic acid-β-(7-amido-4-methylcoumarin)
N-α-Benzoyl-DL-arginine-7-amido-4-methylcoumarin
N-α-Benzoyl-L-arginine-7-amido-4-methylcoumarin
N-Benzoyl-L-phenylalanyl-L-valyl-L-arginine-7-amido-4-methylcoumarin
S-Benzyl-L-cysteine-7-amido-4-methylcoumarin Table III (cont.):
AMC (7-Amido-4-methylcoumarin) Aminopeptidase Substrates
N-BOC-L-phenylalanyl-L-seryl-L-arginine-7-amido-4-methylcoumarin acetate
N-BOC-L-vanyl-glycyl-L-arginine-7-amido-4-methylcoumarin hydrochloride
N-BOC-L-vanyl-L-leucyl-L-lysine-7-amido-4-methylcoumarin Salt
N-α-CBZ-L-arginine-7-amido-4-methylcoumarin hydrochloride
N-CBZ-glycylglycyl-L-leucine-7-amido-4-methylcoumarin
N-CBZ-glycyl-L-proline-7-amido-4-methylcoumarin
N-CBZ-glycyl-L-prolyl-L-arginine-7-amido-4-methylcoumarin
N-β-CBZ-L-lysine-7-amido-4-methylcoumarin
N-CBZ-L-phenylalanyl-L-arginine-7-amido-4-methylcoumarin hydrochloride
N-CBZ-L-prolyl-L-arginine-7-amido-4-methylcoumarin hydrochloride
L-Citrulline-7-amido-4-methylcoumarin hydrochloride
L-Citrulline-7-amido-4-methylcoumarin hydrochloride TFA
D-Glutamic acid-γ-(7-amido-4-methylcoumarin)
L-Glutamic acid-α-(7-amido-4-methylcoumarin)
L-Glutamine-7-amido-4-methylcoumarin hydrochloride
Glutaryl-glycyl-L-arginine-7-amido-4-methylcoumarin hydrochloride
Glutaryl-glycylglycyl-L-phenylalanine-7-amido-4-methylcoumarin
Glutaryl-L-phenylalanine-7-amido-4-methylcoumarin
Glycine-7-amido-4-methylcoumarin hydrochloride
Glycyl-L-alanine-7-amido-4-methylcoumarin hydrochloride
Glycyl-L-arginine-7-amido-4-methylcoumarin Salt
Glycylglycine-7-amido-4-methylcoumarin hydrochloride
Glycyl-L-phenylalanine-7-amido-4-methylcoumarin
Glycyl-L-proline-7-amido-4-methylcoumarin hydrochloride
L-Histidine-7-amido-4-methylcoumarin
L-Isoleucine-7-amido-4-methylcoumarin
L-Isoleucine-7-amido-4-methylcoumarin TFA
L-Leucine-7-amido-4-methylcoumarin
L-Leucine-7-amido-4-methylcoumarin hydrochloride
L-Leucyl-1-valvyl-1-tyrosine-7-amido-4-methylcoumarin
L-Lysine-7-amido-4-methylcoumarin acetate
L-Methionine-7-amido-4-methylcoumarin acetate
L-Ornithine-7-amido-4-methylcoumarin carbonate
L-Phenylalanine-7-amido-4-methylcoumarin TFA
L-Proline-7-amido-4-methylcoumarin hydrochloride
L-Prolyl-L-phenylalanyl-L-arginine-7-amido-4-methylcoumarin Salt
L-Pyroglutamic acid-7-amido-4-methylcoumarin
L-Serine-7-amido-4-methylcoumarin hydrochloride
L-Seryl-L-tyrosine-7-amido-4-methylcoumarin hydrate
L-Tyrosine-7-amido-4-methylcoumarin In one aspect, this invention provides a medium for the detection of yeasts and molds in a sample. In a preferred embodiment the medium contains: (a) one or more aminopeptidase substrates which provide an identical type of detectable signal when hydrolyzed by leucine aminopeptidase and/or alanine aminopeptidase from yeasts and molds; (b) one or more aminopeptidase inhibitors in an amount sufficient to reduce or inhibit endogenous aminopeptidase activities in biological matrices; (c) optimum or sufficient amounts of nutrients including carbohydrates, amino acids, nitrogen sources, vitamins, and trace elements to support growth of the target microbe until a detectable characteristic signal is produced in the medium; and (d) one or more selective agents in an amount sufficient to suppress the growth of bacteria.

In accordance with a preferred embodiment, the enzyme substrates are selected from the group of aminopeptidase substrates consisting of amido-methyl-coumarin (AMC) substrates that are listed in Table III. In a further preferred embodiment, the enzyme substrates include L-leucine 7-amido-4-methylcoumarin and L-alanine 7-amido-4-methylcoumarin. In yet another preferred embodiment, H-leucine-chloromethylketone is provided in amount to inhibit endogenous aminopeptidase activity in biological matrices, e.g., at 0.01 to 0.02 grams per liter of medium.

The invention also provides a method of using the above-described medium to detect yeasts and molds in a test sample. The medium is inoculated with the test sample and incubated under conditions suitable for the growth of yeasts and molds for a certain time period (preferably no more than 72 hours, more preferably no more than 48 hours, even more preferably no more than 24 hours). The production, e.g., of 7-amido-4-methyl-coumarin from an enzyme substrate permits fluorescent emission. The fluorescence, produced by substrate hydrolysis by aminopeptidases, indicates the presence of yeasts and molds in the test sample. The test medium does not have to be kept sterile, but obviously must be free of viable target microbes.

In a preferred embodiment, the medium is comprised in a powder form. The powder is preferably liquefied with sterile water before a test sample is inoculated with the medium. The incubation may be performed at a temperature either at 25° C. or at 30° C.

The term "liquefied" means substantially in liquid form, though it is also meant to include pulverized or homogenized samples of solid substances having at least a 10% liquid content. Liquefied medium is distinct from a gelled medium, such as is found with agar-based medium.

In another preferred embodiment, the method uses a gelled medium. A preferred gelled medium is an agar medium that comprises one or more aminopeptidase substrates.

In yet another aspect, the invention provides a method for quantifying the number of yeasts and molds present in a sample. In this aspect, the invention is a method to enumerate the amount of yeasts and molds in a sample by contacting the sample with the subject medium, placing the sample and medium mixture in containers, incubating the sample and medium mixture, observing the quantity and quality of detectable characteristic signals, and comparing the quantity of detectable characteristic signals with most probable number values. This quantifying process comprises comparing the quantity and quality of the characteristic which has been altered, preferably a color change, or even more preferably a fluorescence change, to a statistically determined most probable number. Such statistical determinations take place in accordance with the methodologies known to those in the art. The most probable number (MPN) technique is based on probability statistics. The results from any type of an MPN analysis are directly related to the frequency of occurrence of a series of positive results that are most likely to occur when certain numbers of organisms are present in a sample.

The composition of the invention is added to medium which is preferably used to conduct assays in multiwell microtiter plates. In preferred embodiments, the invention is used with the apparatus described by Croteau et al. in U.S. Ser. No. 08/557,529, or that described by Croteau, et al. in U.S. Ser. No. 08/606,229, each of which are hereby incorporated by reference; assay devices incorporating such technology are marketed under the tradename SimPlate™ (IDEXX Laboratories, Westbrook, Me.). The quantifying step preferably involves providing a sample of an environmental or biological sample into a liquefied medium of the invention, placing or dispensing the mixture of sample and medium into a device described by Croteau et al., incubating the sample, detecting the quantity and quality of the detection moiety characteristic, and optionally comparing the quantity of the characteristic signal with most probable number (MPN) values. Preferably, the incubation step is carried out at 25° C. for a period of 72 hours using the medium described above. Even more preferably, the incubation step is carried out at 30° C. for a period of 48 hours using the medium described above.

Using the media and methods of this invention, yeast and mold concentration in a test sample can be determined much easier and faster than by methods currently available. For example, the invention can be used in quality control testing for food products and for other contexts in which one wishes to determine the presence or quantity of yeasts and/or molds. Rapid and easy testing allows manufacturers to release products without scarifying product quality and integrity. Easy testing and rapid results represent significant labor and economical savings for the laboratory and the manufacturers and significant benefits for consumers.

Components of the Yeast and Mold Growth Medium

A "media" of the invention can be a solid, powder, or liquid mixture which comprises all or substantially all of the nutrients necessary to support the growth of yeasts and molds; various nutrient compositions are preferably prepared when particular mold or yeast species are being assayed. Amino acids, carbohydrates, minerals, vitamins and other elements known to those skilled in the art to be necessary for the growth of yeasts and molds are provided in the medium. In a preferred embodiment, the medium is liquid. In another preferred embodiment, the medium is agar-based and can be in gelled form. In yet another preferred embodiment, the medium is in the form of a reconstitutable powder, which upon reconstitution allows growth and detection of yeasts and molds. The medium of this invention is free of viable yeasts and molds; otherwise, it may be either sterile or non-sterile.

A media composition which has proven advantageous in this invention for detecting the presence of yeasts and molds in a test sample comprises a buffer, a nitrogen source and other nutrient components required for the growth and metabolic activity of yeasts and molds.

For example, the buffer can be comprised of (per liter): (2-[N-Morpholino]ethanesulfonic acid)—free acid (e.g. about 4.1 to 9.8 grams), (2-[N-Morpholino]ethanesulfonic acid)—sodium salt (e.g. about 5.5 to 13.2 grams).

The nitrogen source can be (per liter), ammonium sulfate (about 4 to 6 grams).

A presently preferred composition for detecting yeasts and molds is described in Table IV.

TABLE IV

| Media Components | | |
|---|---|---|
| Amino Acid Components | | |
| Ingredients | Preferred Amount (grams/liter) | Preferred Range (grams/liter) |
| Alanine | 0.599 | 0.4792–0.7188 |
| Arginine | 0.549 | 0.4392–0.6588 |
| Aspartic acid | 0.692 | 0.5536–0.8304 |
| Glutamic acid | 1.238 | 0.9904–1.494 |
| Glycine | 0.926 | 0.7408–0.1112 |
| Histidine | 0.184 | 0.1472–0.2208 |
| Isoleucine | 0.265 | 0.212–0.318 |
| Cystine | 0.112 | 0.0896–0.1344 |
| Leucine | 0.57 | 0.456–0.684 |
| Lysine | 0.502 | 0.4016–0.6024 |
| Methionine | 0.206 | 0.1648–0.2472 |
| Phenylalanine | 0.272 | 0.2176–0.3264 |
| Proline | 0.494 | 0.3952–0.5928 |
| Serine | 0.365 | 0.292–0.438 |
| Threonine | 0.332 | 0.2656–0.3984 |
| Tryptophan | 0.079 | 0.0632–0.0948 |
| Tyrosine | 0.196 | 0.1568–0.2352 |

TABLE IV-continued

Media Components

| | | |
|---|---|---|
| Valine | 0.362 | 0.2896–0.4344 |

Vitamin and Element Components

| Ingredients | Source | Preferred Amount (mg/liter) | Preferred Range (mg/liter) |
|---|---|---|---|
| Vitamins | biotin | 0.006 | 0.002–0.01 |
| | chlorine | 37 | 18–54 |
| | Cyanocobalamin | trace* | trace |
| | pantothenic acid | 0.6 | 0.01–1 |
| | folic acid | 0.003 | 0.0001–0.005 |
| | inositol | 91 | 50–200 |
| | niacin | 0.4 | 0.1–1 |
| | p-aminobenzoic acid | 0.2 | 0.01–0.05 |
| | pyridoxine hydrochloride | 0.413 | 0.1–1 |
| | riboflavin | 5.268 | 0.5–10 |
| | thiamine hydrochloride | 100.4 | 50–200 |
| Elements | calcium | 2.3 | 1.84–2.76 |
| | chloride | 358 | 286–430 |
| | cobalt | 0.1 | 0.01–0.2 |
| | iron | 0.1 | 0.01–0.2 |
| | lead | 0.1 | 0.01–0.2 |
| | manganese | 2.7 | 2.0–3.3 |
| | phosphorus | 145 | 115–175 |
| | potassium | 98 | 80–120 |
| | sulfur | 120 | 60–180 |
| | sodium | 392 | 310–470 |
| | tin | 0.1 | 0.01–0.2 |
| | zinc | 0.7 | 0.5–0.9 |

Additional Components

| Ingredients | Preferred Amount (grams/liter) | Range (grams/liter) |
|---|---|---|
| Mes, free acid | 8.2 | 4.1–9.8 |
| MES, sodium salt | 11 | 5.5–13.2 |
| Ammonium sulfate | 5 | 4–6 |
| D-glucose | 5 | 1–10 |
| D-fructose | 10 | 1–10 |
| Adenine hydrochloride | 0.1 | 0.01–0.02 |
| 2,6-Dichloro-4-nitroaniline | 0.002 | 0.001–0.002 |
| Potassium phosphate, monobasic | 1 | 0.8–1.2 |
| Magnesium sulfate | 0.5 | 0.25–0.75 |
| Sodium chloride | 0.1 | 0.01–0.2 |
| Calcium chloride | 0.1 | 0.01–0.2 |
| Boric acid | 0.0005 | 0.0001–0.01 |
| Copper sulfate | 0.00004 | 0.00001–0.01 |
| Potassium Iodide | 0.0001 | 0.00001–0.01 |
| Ferric chloride | 0.0002 | 0.00001–0.01 |
| Manganese sulfate | 0.0004 | 0.0001–0.01 |
| Sodium molybdate | 0.0002 | 0.00001–0.01 |
| zinc sulfate | 0.0004 | 0.0001–0.01 |
| L-leucine-chloromethyl-ketone | 0.016 | 0.01–0.02 |
| L-leucine 7-amido-4-methylcoumarin | 0.025 | 0.015–0.03 |
| L-alanine 7-amido-4-methylcoumarin | 0.025 | 0.015–0.03 |
| Gentamicin sulfate | 0.05 | 0.025–0.075 |
| Chloramphenicol | 0.1 | 0.05–0.15 |

In addition, the following components are provided in the medium in approximately the amounts indicated. Those skilled in the art will understand that not every component is required. Components may also be substituted with other components of similar properties. The amounts of components may also vary. The additional components can comprise:

Carbohydrates:

One of the most important classes of nutrients for yeasts and molds is carbohydrates which serve as a source of carbon and energy. Degradation of carbohydrates yields simple sugars (e.g. glucose, fructose, or mannose) which enter the glycolytic pathway and tricarboxylic acid cycle. To provide a carbon source for yeasts and molds, carbohydrates may be provided from various sources. As is known in the art that different species of yeasts and molds may have different carbohydrate requirements.

Those skilled in the art will also recognize that various sources of carbohydrates can be used. They can be natural sources (e.g., potato or plant extracts), as mixtures of natural sources, in pure forms (such as oligosaccharides or monosaccharides), in mixtures of pure forms, or as mixture of pure and natural forms. The natural mixtures can contain varying amounts of carbohydrates. Thus, carbohydrates may be provided from a variety of sources.

The natural mixtures can contain various types and amounts of carbohydrates, such as polysaccharides, oligosaccharides, and monosaccharides. Polysaccharides that can be assimilated by yeasts and molds include soluble starch or inulin. Oligosaccharides that can be assimilated by yeasts and molds are sucrose, maltose, cellobiose, trehalose, lactose, melibiose, raffinose, and melezitose. Monosaccharides that can be metabolized by yeasts and molds include the hexoses (six carbon sugars): e.g., D-glucose, D-fructose, D-galactose, D-mannose, L-rhamnose, and L-sorbose; as well as the pentoses (five carbon sugars): e.g., D-xylose, D-ribose, L-arabinose, and D-arabinose. In general, glucose, fructose, and mannose can be utilized by all yeasts and molds, but there are great differences among the species with respect to utilization of these sugars.

Not all carbohydrates must be provided and the relative amount of each may vary. Those in the art will recognize that many different combinations of monosaccharides can be used in the medium of this invention. Normally, only the sugars that can be metabolized by yeasts and molds are provided.

In general, glucose, fructose, and mannose can be utilized by all yeasts and molds, but there are great differences among the species with respect to utilization of these sugars.

For general guidance, specific amounts of carbohydrates are indicated below. These amounts are for general guidance only, and are determinable in accordance information known to those of skill in the art, and are not limiting in this invention. Those in the art will recognize that many different combinations of carbohydrates can be used in media of this invention. The list provided below exemplifies just one such example. Normally, only those sugars which can be utilized by any particular yeasts and molds to be detected must be provided. Those skilled in the art will appreciate that other carbohydrates may be provided without departing from the invention. Thus, in a preferred embodiment, the medium of this invention contains D-glucose (about 1 to 10 grams/liter) and D-fructose (about 1 to 10 grams/liter).

Amino Acids:

Amino acids required for the growth and metabolic activity of yeasts and molds are provided. Not all amino acids must be provided and the relative amount of each may vary. Amino acids may be provided from a variety of sources. Those in the art will recognize that natural sources of amino acids can be used as can pure sources, or any combination thereof.

Thus, amino acids may be provided from a variety of sources. These can be provided from natural sources (e.g. extracts of organisms or plants), either as mixtures, or in purified form. The natural mixtures may contain varying amounts of amino acids and/or vitamins. Not all amino acids must be provided, and the relative amount of each can vary. For general guidance, specific amounts of amino acids and vitamins are indicated below. These amounts are for guidance only and are not limiting in this invention. Those in the art will recognize that many different combinations of amino acids and vitamins can be used in the medium of this invention.

The list provided below exemplifies just one preferred embodiment, e.g., with variations based on the metabolic characteristics of a particular yeast or mold being detected (if a particular yeast or mold contaminant is identified). Normally, only those amino acids which cannot be synthesized indigenously by yeasts and molds to be detected must be provided. However, other amino acids may be provided without departing from the medium of the invention.

The medium preferably includes at least the following amino acids in approximately the following amounts (per liter of medium): alanine (0.4792 to 0.7188 grams), arginine (0.4392 to 0.6588 grams), aspartic acid (0.5536 to 0.8304 grams), glutamic acid (0.9904 to 1.494 grams), glycine (0.7408 to 0.1112 grams), histidine (0.1472 to 0.2208 grams), isoleucine (0.212 to 0.318 grams), cystine (0.0896 to 0.1344 grams), leucine (0.456 to 0.684 grams), lysine (0.4016 to 0.6024 grams), methionine (0.1648 to 0.2472 grams), phenylalanine (0.2176 to 0.3264 grams), proline (0.3952 to 0.5928 grams), serine (0.292 to 0.438 grams), threonine (0.2656 to 0.3984 grams), tryptophan (0.0632 to 0.0948 grams), tyrosine (0.1568 to 0.2352 grams), and valine (0.2896 to 0.4344 grams).

Vitamins:

Vitamins required for growth and reproduction of yeasts and molds sought to be detected may also be provided. These can be provided in a pure form or as part of natural extracts or any combination thereof. The natural mixtures may contain varying amounts of amino acids and/or vitamins.

In one embodiment, vitamins may be present in approximately the following amounts (per liter of medium): biotin (about 2 to 10 $\mu$g), chlorine (about 18 to 54 mg), pantothenic acid (about 10 to 1000 $\mu$g), folic acid (about 0.1 to 5 $\mu$g), inositol (about 50 to 200 mg), niacin (about 100 to 1000 $\mu$g), para-aminobenzoic acid (about 10 to 50 $\mu$g), pyridoxine hydrochloride (about 100 to 1000 $\mu$g), riboflavin (about 0. 5 to 10 mg), thiamine hydrochloride (about 50 to 200 mg), and trace amount (less than 10 $\mu$g) of cyanocobalamin.

Selective Agents:

One or more selective agents (e.g., antibiotics) which prevent the growth of viable heterotrophic bacteria whose presence is not sought to be determined is preferably provided in the medium (per liter of medium) in an amount of 50 to 200 milligrams. Many other selective agents can also be provided; the agent(s) chosen depending upon which microbes are targets of the assay.

Typical selective agents useful in the medium of this invention to prevent the growth of heterotrophic bacteria that possess either L-leucine aminopeptidase or L-alanine aminopeptidase activity include: chlorotetracycline (Aureomycin), chloramphenicol, oxytetracycline, gentamicin, streptomycin, kanamycin, vancomycin, amikacin, polymyxin, colistin, neomycin, and cefotaxime. The selective agents presently preferred in the medium of this invention are chloroamphenicol (about 0.050 to 0.125 g/liter) and gentamicin (about 0.025 to 0.075 glliter); most preferably these two antibiotics are provided in combination.

Trace Elements:

Other inorganic trace elements may be included to aid in the growth of yeasts and molds. These include the following (to the extent not already provided in the above sources of various media entities, these are described in amounts per liter): calcium (about 1.84 to 2.76 mg), chloride (about 286 to 430 mg), cobalt (about 0.01 to 0.2 mg), iron (about 0.01 to 0.2 mg), lead (about 0.01 to 0.2 mg), manganese (about 2.0 to 3.3 mg), phosphorus (about 115 to 175 mg), potassium (about 80 to 120 mg), sulfur (about 60 to 180 mg), sodium (about 310 to 470 mg), tin (about 0.01 to 0.2 mg), and zinc (about 0.5 to 0.9 mg).

Salts:

Salts may be provided as a source of ions. Salts may include (amounts per liter of medium): potassium phosphate (about 0.8 to 1.2 grams), magnesium sulfate (about 0.25 to 0.75 grams), sodium chloride (about 0.01 to 0.2 grams), calcium chloride (about 0.01 to 0.2 grams), boric acid (about 0.0001 to 0.01 grams), copper sulfate (about 0.00001 to 0.01 grams), potassium iodide (about 0.00001 to 0.01 grams), ferric chloride (about 0.00001 to 0.01 grams), manganese sulfate (about 0.00001 to 0.01 grams), sodium molybdate (about 0.00001 to 0.01 grams), and zinc sulfate (0.00001 to 0.01 grams).

Growth Stimulators:

The medium may contain agents which act as a metabolic stimulator to enhance metabolic activity of yeasts and molds. Preferably, the medium of this invention contains adenine hydrochloride (about 0.01 to 0.2 grams/liter). The medium may also contain agents which function as the secondary message in the signal transduction pathway to thereby stimulate proliferation of yeasts and molds. Such agents include D-fructose-2,6-diphosphate which enhances the metabolic activity in the glycolytic pathway, and phosphoinositides which stimulate cell proliferation through a signal transduction cascade.

Unsaturated fatty acids such as elaidic acid, eracic acid, nervonic acid, petroselinic acid may be incorporated into the medium to stimulate the growth of yeasts and molds.

Enzyme Inhibitors:

A problem often encountered in designing an enzyme-based microbial detection system, and overcome by the present invention, is signal interference due to substrate hydrolysis by endogenous enzymes in the biological matrices. Thus, an objective is to prevent or reduce signal interference from the endogenous enzyme activity in biological matrices. However, a factor that limits the ability to reduce signal interference is that the inhibition should not interfere with result interpretation. This challenge is not easily met because different biological matrices contain different levels of endogenous enzyme activity.

In another aspect, this invention can comprise a medium which inhibits or reduces endogenous enzyme activities in biological matrices. According to this invention, effective amounts of enzyme inhibitors are added to a microbial growth medium to suppress endogenous enzyme activity, so that one can measure microbial concentration as a function of microbial enzyme activities. The enzyme inhibitors include, but are not limited to, the inhibitors for, phosphatases, glucosidases, glucuronidases, galactosidases, esterases, aminopeptidases, and proteases.

For samples having levels of endogenous enzymatic activity that would interfere with an assay result in accordance with the invention, the presence of microorganisms will only be detected by revealing microbial enzyme activities apart from the endogenous activity in a biological matrix. The list is not meant to exclude other enzyme inhibitors which have yet to be discovered but are useful for similar applications. As appreciated by one of ordinary skill in the art in view of the present disclosure, other enzyme inhibitors can be included for such application; such other enzymes can be those presently known or yet to be discovered.

In a preferred embodiment, the enzyme inhibitor included in the yeast/mold specific medium is a compound operable to inhibit or reduce the endogenous aminopeptidase activities in food matrices. In preferred embodiments, the aminopeptidase inhibitor incorporated in the growth medium can comprise one or more of the following:

H-leucine-chloromethylketone,
phenylmethylsulfonyl fluoride,
Tos-Lys-chloromethylketone,
Ac-Leu-Leu-methioninal,
Ac-Leu-Leu-norleucinal,
Ac-Leu-Val-lysinal,
Eglin c(42–54)-methyl ester,
H-Ala-Ala-Phe-chloromethylketone,
H-Ala-Ala-Pro-Val-chloromethylketone,
Boc-Asp(OBzl)-chloromethylketone,
Boc-Leu-chloromethylketone,
H-Glu-Gly-Arg-chloromethylketone.

The above list provides the presently preferred inhibitors. It is understood that this list does not exclude other known aminopeptidase inhibitors or those which have yet to be discovered and included in this list by those of ordinary skill in the art. In a further preferred embodiment, the aminopeptidase inhibitor incorporated in the yeast/mold specific growth medium is H-leucine-chloromethylketone, at about 0.010 to 0.020 g/liter.

Amounts of Materials in a Composition of the Invention

Those in the art will recognize that buffer ingredients, carbon, nitrogen, trace elements, vitamins, amino acids, selective agents, growth stimulators and enzyme inhibitors can be provided in many forms. Generally, it is preferred to have amounts as provided herein, but those in the art will recognize that the actual properties of each ingredient may be varied so that a reduction in the amount of one ingredient can be compensated by an increase in the amount of another. This is particularly relevant when the essential amino acids, trace elements, or vitamins of the microbes sought to be detected are known, i.e., non-essential nutrients can be omitted. Further, some ingredients may be provided in reduced amounts or deleted if they may be synthesized endogenously by yeasts and molds.

Detecting Yeasts and Molds Based on Aminopeptidase Activities

One approach to test the presence of a microorganism or a group of microorganisms is to take advantage of the metabolic and physiological characteristics of specific microbes. Specific microorganisms derive their nutrients from an array of sources, some of which may be unique to a particular microorganism or group of microorganisms. Many enzymes have been identified which are specific to particular groups or species and others likely will be identified in the future.

A method for detecting either or both yeasts and molds in a test sample preferably comprises measuring the activity of L-leucine aminopeptidase, or L-alanine aminopeptidase, or even a combination of both enzymes. Two presently preferred aminopeptidase substrates used in detecting yeasts and molds are L-leucine 7-amido-4-methyl coumarin (about 0.015 to 0.050 g/liter) and L-alanine 7-amido-4-methyl coumarin (about 0.015 to 0.050 g/liter.)

Preferably, the yeast and/or mold assay is done in an environment selective for the growth of yeasts and molds. In addition to yeasts and molds, some heterotrophic bacteria (including both gram positive and negative bacteria) possess aminopeptidase activity. In one embodiment, such bacteria are suppressed by a combination of specifically formulated selective agents (e.g., chemicals and/or antibiotics) and other physical parameters (e.g., pH or incubation temperature).

One common problem encountered in enumerating yeasts and molds in a sample by the traditional plating techniques is that the predominate mycelial growth of certain molds prevents accurate enumeration of the viable cells. A preferred embodiment of a medium of this invention incorporates 2,6-Dichloro-4-nitroaniline (Dichloran) (about 2 mg/liter) to restrict the mycelial growth of mold colonies. Dichloran only restricts mycelial growth, i.e., it prevents the spreading of molds on a culture plate. It normally makes molds grow in an upward direction and therefore prevents the spreading problem that can interfere with result interpretation.

Assay Temperature

In a preferred embodiment, the time required for the test sample containing yeasts and molds to display detectable characteristic changes is 48 hours; in this embodiment, the assay is conducted at 30° C. Alternatively, when the assay is conducted at 25° C., a result is obtained in 72 hours.

It should be noted that the amount of oxygen and carbon dioxide in the medium, amount and type of enzyme substrates present, amount and type of enzyme inhibitors and selective agents present, amount and types of nutrients provided in the medium, and the relative health of yeasts and molds all affect the detection time. The amount of nutrients such as carbohydrates, amino acids, vitamins, and trace elements provided may affect growth rate of the target microbe and thus detection. The amounts of growth stimulators may also decrease the time to detection. Adding agents such as pyruvate may aid recovery of injured organisms may therefore speed detection. If large numbers of yeast and mold are present in the sample, more rapid detection is generally possible.

In this invention, the medium provided allows detection of high number of target microbes in as early as 24 hours at either 25° C. or 30° C. In the embodiment of the invention conducted at 30°, the medium provides enumeration of yeasts and molds within 48 hours; this detection provides counts equivalent to the counts obtained from the traditional plating methods which took five days. The correlation coefficient between the present method and the plating methods is greater than or equal to 0.9.

Other features and advantages of the invention will be apparent from the following examples and from the claims.

EXAMPLES

Example 1

A total of 101 fungal isolates obtained from different food matrices including meat-containing burrito prepared from store-bought ingredients, ground beef, ground pork, beverage (fruit juices and carbonated soft drink) were examined for their ability to hydrolyze different enzyme substrates in pH 7.0, 50 mM HEPES buffer.

Nine different fluorogenic enzyme substrates were prepared as 100 mM stock solution in pH 7.0, 50 mM HEPES buffer.

A 2 milliliter aliquot of fungal culture suspension (approximate $10^6$ cfu/ml) was added to individual microliter wells. For each well, a 50 microliter of the enzyme substrate stock solution was added to the culture suspension. The plate was incubated at 30° C. Fluorescence signal was observed by using a long wavelength ultraviolet lamp (365 nm) after 1 and 24 hours of incubation.

| | | Enzyme Substrate Utilization by Fungal Isolates | | | | | | | | | | | | | | | | | |
|---|---|---|---|---|---|---|---|---|---|---|---|---|---|---|---|---|---|---|---|
| | | # Isolates Positive @ 1 Hours Fluorogenic Substrate (1–9) | | | | | | | | | # Isolates Positive @ 24 Hours Fluorogenic Substrate (1–9) | | | | | | | | |
| Fungi Source | # Isolates | 1 | 2 | 3 | 4 | 5 | 6 | 7 | 8 | 9 | 1 | 2 | 3 | 4 | 5 | 6 | 7 | 8 | 9 |
| Burrito | 7 | 0 | 5 | 0 | 0 | 0 | 0 | 7 | 7 | 7 | 0 | 7 | 0 | 0 | 0 | 0 | 7 | 7 | 7 |
| Ground Beef | 35 | 7 | 4 | 0 | 0 | 0 | 0 | 17 | 31 | 28 | 11 | 12 | 6 | 8 | 3 | 0 | 24 | 35 | 35 |
| Chicken | 9 | 0 | 0 | 0 | 0 | 0 | 0 | 0 | 9 | 9 | 0 | 0 | 0 | 0 | 0 | 0 | 6 | 9 | 9 |
| Ground Pork | 16 | 0 | 2 | 0 | 0 | 0 | 0 | 0 | 15 | 16 | 0 | 2 | 0 | 0 | 0 | 0 | 14 | 16 | 16 |
| Corned Beef | 5 | 1 | 1 | 0 | 0 | 0 | 0 | 1 | 5 | 5 | 0 | 3 | 5 | 3 | 3 | 0 | 5 | 5 | 5 |
| Beverage | 29 | 8 | 7 | 0 | 0 | 0 | 0 | 4 | 28 | 28 | 17 | 26 | 3 | 3 | 9 | 0 | 9 | 29 | 29 |
| Total | 101 | 16 | 19 | 0 | 0 | 0 | 0 | 29 | 100 | 100 | 28 | 50 | 14 | 14 | 12 | 0 | 85 | 101 | 101 |

Fluorogenic Substrates (1–9)
1. 4-Methylumbelliferyl-α-D-glucopyranoside (substrate for α-glucocidase)
2. 4-Methylumbelliferyl-β-D-glucopyranoside (substrate for β-glucosidase)
3. 4-Methylumbelliferyl-N-acetyl-β-D-glucosamine (substrate for N-acetyl-β-glucosamidase)
4. 4-Methylumbelliferyl-β-D-cellobiose (substrate for β-D-cellobiosidase)
5. 4-Methylumbelliferyl-β-D-xylose (substrate for β-D-xylosidase)
6. 4-Methylumbelliferyl-β-D-mannose (substrate for β-D-mannosidase)
7. 4-Methylumbelliferyl-phosphate (substrate for phosphatase)
8. L-leucine-7-Amido-4-methylcoumarin (substrate for L-leucine aminopeptidase)
9. L-Alanine-7-Amido-4-methylcourmarin (substrate for L-alanine aminopeptidase)

Results indicated that 99% of the fungal isolates hydrolyzed both L-leucine-7-amido-4-methylcoumarin and L-alanine-7-amido-4-methylcoumarin at 1 hour, and 100% of the isolates hydrolyzed these substrates at 24 hours. These results indicated that L-leucine aminopeptidase and L-alanine aminopeptidase are ubiquitously present in yeasts and molds. Based on this discovery, these enzymes were chosen as the target enzymes for detecting yeasts and molds in accordance with this invention.

Other enzymes are present in a much smaller percentage of the isolates, e.g., 64% for phosphatase, 50% for β-glucosidase, and 28% for α-glucosidase, respectively. These enzymes are, therefore, not suitable to be used as the target enzyme(s) for the detection of total yeasts and molds.

Example 2

Assays on solid food samples were performed in accordance with the following methodology:

Sample Preparation
1. 25 grams of a solid food product was weighed into a sterile stomach bag,
2. 225 ml of a sterile diluent (e.g., Butterfield's buffer or 0.1% peptone water) were then added into the stomach bag which contained grams of the food product.
3. The stomach bag containing both food sample and diluent were placed to a stomacher and were stomached for 2 minutes at normal setting (this stomached food homogenate represents $10^{-1}$ dilution).
4. 11 ml of the $10^{-1}$ dilution were added to 99 ml sterile diluent (This represents $10^{-2}$ dilution).
5. 11 ml of the $10^{-2}$ dilution were added to 99 ml sterile diluent (This represents $10^{-3}$ dilution.).

Test Procedure
Step 1. Inoculation
1. $10^{-1}$ dilution Inoculum
A 1 ml aliquot of the $10^{-1}$ dilution was placed on a multiwell microtiter plate; when SimPlates were used, the aliquot was placed in the center of the landing pad of the SimPlate (labeled as $10^{-1}$),
2. $10^{-2}$ dilution Inoculum
A 1 ml aliquot of the $10^{-2}$ dilution was placed on a multiwell microtiter plate; when SimPlates were used, the aliquot was placed in the center of the landing pad of the SimPlate (labeled as $10^{-2}$),
3. $10^{-3}$ dilution Inoculum
A 1 ml aliquot of the $10^{-3}$ dilution was placed on a multiwell microtiter plate; when SimPlates were used, the aliquot was placed in the center of the landing pad of the SimPlate (labeled as $10^{-3}$).

Step 2. Add Medium
In the studies we conducted, four plates were used for each dilution: two plates for 25° C. assays and two plates for 30° C. assays.
1. A 9 ml aliquot of the prepared medium of the invention was placed in a test well of a microtiter plate; when SimPlates were used, medium of the invention was placed in the center of the landing pad that already contained the sample inoculum.
2. The plate was gently swirled in a clockwise and then counterclockwise motion to distribute the liquid into the wells (excessive force was avoided when mixing as this can cause air bubbles which may prevent proper medium distribution).
3. It was verified that the wells are filled. When SimPlates were used, a notch on the lid was lined with the pour spout on the base and excess liquid was gently poured off the by holding the SimPlate at an approximately 90 degree angle with the pour spout facing down. (It was not a problem if a couple drops of liquid remained in the SimPlate after pour off).
4. This procedure was repeated with other samples. The trays were gently stacked on top of each other (SimPlates should not be stacked more than 10 high).

Step 3. Incubation
1. For assays at 25° C., the plates were incubated in a 25° C. incubator for 3 days; for assays at 30° C., the plates were incubated in a 30° C. incubator for 2 days. (The plates should not be inverted.)

Step 4. Count Plates
1. 30° C. Incubation
At 48±2 hours, plates were removed from the 30° C. incubator.
The number of wells exhibiting blue fluorescence were examined by placing under a long wavelength UV lamp (any fluorescent wells should be considered as positive wells); the number of wells showing blue fluorescence were recorded. Fluorescent signal was more distinct under the low light conditions; preferably in the dark. SimPlates were counted with the lid on.

The CFU/plate was determined by looking at a MPN chart indicating the CFU/plate vs. # positive fluorescent wells.

Certain molds may grow to such an extend that a well is covered, and the fluorescent signal is quenched. If the mold was visually obvious, this was countered as a positive well.

2. 25° C. Incubation

At 72±2 hours, plates were removed from the 25° C. incubator in accordance with the procedure described for 30° C. incubation.

Example 3

Assays on liquid food samples were performed in accordance with the following methodology:

Sample Preparation

1. A liquid food sample was placed in a sterile container or equivalent (this original liquid food sample represented a $10^0$ dilution),
2. 11 ml of the $10^0$ dilution aliquot was added to 99 ml of a sterile diluent (e.g., Butterfield's buffer or 0.1% peptone water) (labeled 10–1 dilution),
3. 11 ml of the $10^{-1}$ dilution aliquot was added to 99 ml of a sterile diluent (labeled $10^{-2}$ dilution).

Test Procedure

Step 1. Inoculation

1. $10^0$ dilution Inoculum

A 1 ml aliquot of the $10^0$ dilution (original liquid food sample) was placed in a multiwell microtiter plate; when SimPlates were used, the aliquot was placed in the center of the landing pad of the SimPlate (labeled as $10^0$), 2. $10^1$ dilution Inoculum A 1 ml aliquot of the $10^1$ dilution was placed in a multiwell microtiter plate; when SimPlates were used the aliquot was placed in the center of the landing pad of the SimPlate (labeled as $10^1$)

3. $10^2$ dilution Inoculum

A 1 ml aliquot of the $10^2$ dilution was placed in a multiwell microtiter plate; when SimPlates were used the aliquot was placed in the center of the landing pad of the SimPlate (labeled as $10^2$).

Step 2. Add Medium

In the studies we conducted, four plates were used for each dilution: two plates for 25° C. assays and two plates for 30° C. assays.

1. A 9 ml aliquot of the prepared medium of the invention was added to the microtiter plate that already contained the sample inoculum.
2. The plate was swirled gently in a clockwise and then counterclockwise motion to mix and distribute the liquid into the wells (excessive force was avoided when mixing, as this could cause air bubbles which may prevent proper medium distribution).
3. It was verified that the wells are filled. When SimPlates were used, a notch on the lid was lined with the pour spout on the base and excess liquid was gently poured off the by holding the SimPlate at an approximately 90 degree angle with the pour spout facing down. (It was not a problem if a couple drops of liquid remained in the SimPlate after pour off.).
4. This procedure was repeated with other samples. The trays were gently stacked on top of each other (SimPlates should not be stacked more than ten high.).

Step 3. Incubation

1. For assays at 25° C., plates were incubated in a 25° C. incubator for 3 days; for assays at 30° C., plates were incubated in a 30° C. incubator for 2 days. Plates should not be inverted.

Step 4. Count Plates 1. 30° C. incubation

At 48±2 hours, plates were removed from the 30° C. incubator. To count the number of wells exhibiting blue fluorescence, plates were placed under a long wavelength UV lamp (any fluorescent wells were considered as positive); the number of wells showing blue fluorescence were recorded. Fluorescent signal was more distinct under the low light conditions; preferably in the dark. SimPlates were counted the with the lids on.

The CFU/plate was determined by looking at the MPN chart indicating the CFU/plate vs. # positive fluorescent wells.

Certain molds grew to the extent a well was covered and the fluorescence signal was quenched. However, if mold was visually obvious, this was counted as a positive well.

2. 25° C. incubation At 72±2 hours, plates were removed from the 25° C. incubator in accordance with the procedure described for 30° C. incubation immediately above.

Example 4

A presently preferred medium of this invention was evaluated in parallel with the standard 5-day Potato Dextrose Agar (PDA) supplemented with chlortetracycline (100 μg/ml) and chloramphenicol (100 μg/ml). The apparatus of Croteau et al., as set forth in U.S. Ser. No. 08/557,529, or in U.S. Ser. No. 08/606,229, was used in conjunction with the medium of this invention to enumerate fungal concentration in food. The presence of yeast and mold in the medium was revealed by blue fluorescence under a long wavelength ultraviolet lamp (365 nm).

Solid food samples were tested in accordance with the protocol set forth in Example 2; liquid food samples were tested in accordance with the protocol set forth in Example 3. Food samples tested included fruit juices (e.g. cranberry juice concentrate, orange pineapple juice concentrate, grape fruit juice concentrate, apple juice concentrate, tomato juice, carbonated soda, ice tea, strawberry concentrate, kiwi punch concentrate, orange juice, papaya, raspberry juice, root beer, and vegetable juice), ingredients (e.g. natural seasoning, black pepper, waffle mix, flour, yellow corn meal, pie filler, soy flour, soy sauce, cake mix, coconut, onion powder, etc.), dairy products (e.g. raw milk, cheddar cheese, sour cream, ice cream, yogurt, etc.), and other prepared food products (e.g. ketchup, pickles, olives, salad dressing, coffee beans, pecans, potato powder, wheat cereal, tea bag, tea mix, etc.).

This embodiment of a medium of this invention, when incubated at 30° C. for 2 days, showed a strong agreement with standard PDA yeast and mold counts (5 days @ 25° C.) with a correlation coefficient of 0.96. Furthermore, a strong linear correlation (r=0.97) was also obtained between an assay of the invention (3 days @ 25° C.) and the 5-day PDA counts (25° C. incubation).

Closing

In the foregoing description, reference is made to various methods known to those skill in the chemical, biological and microbiological arts. Publications and other materials setting forth such known methodologies to which reference is made are incorporated herein by reference in their entireties as though set forth in full.

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific D terms used herein have the same meaning as commonly understood by one of ordinary skill in the art to which this invention belongs. Although any methods and materials similar to or equivalent to those described herein can be used in the practice or testing of the invention, the preferred methods and materials are now described. All publications mentioned herein are incorporated herein by reference to describe and disclose specific information for which the reference was cited in connection with.

What is claimed is:

1. A composition for use in a medium for detecting yeasts and molds in a test sample comprising:
   a) a substrate for an aminopeptidase, wherein a signal moiety is linked to the substrate and said moiety is capable of providing a detectable signal when cleaved by said aminopeptidase in yeasts or molds:
   b) an antibiotic capable of inhibiting the growth of bacteria in said sample; and
   c) an inhibitor of aminopeptidase endogenous to the test sample in an amount effective to suppress endogenous aminopeptidase activity in said sample suspected of containing yeasts or molds.

2. The composition of claim 1, wherein said the enzyme inhibitor is H-leucine-chloromethylketone.

3. The composition of claim 1, wherein said aminopeptidase is L-leucine aminopeptidase or L-alanine aminopeptidase.

4. The composition of claim 3, wherein said substrate comprises a substrate of L-leucine aminopeptidase or L-alanine aminopeptidase, respectively.

5. The composition of claim 4, wherein said one of said substrates is hydrolyzed by L-leucine aminopeptidase, and the other said substrate is hydrolyzed by L-alanine aminopeptidase.

6. The composition of claim 3, wherein said enzyme substrate is L-leucine 7-amido-4-methylcoumarin, L-leucine β-naphthylamide, L-alanine 7-amido-4-methylcoumarin, or L-alanine β-naphthylamide.

7. The composition of claim 1, wherein said signal moiety is ortho-nitrophenyl, 4-methylumbelliferone, para-nitroanilide, 4-methoxy-β-naphthylamide, 7-amido-4-methylcoumarin.

8. The composition of claim 1, wherein said enzyme substrate is: N-o-Acetyl-lysine-7-amido-4-methylcoumarin acetate; N-Acetyl-L-phenylalanyl-L-arginine-7-amido-4-methylcoumarin hydrochloride; L-Alanine-7-amido-4-methylcoumarin; β-Alanine-7-amido-4-methylcoumarin TFA; D-Alanine-7-amido-4-methylcoumarin TFA; L-Alanine-7-amido-4-methylcoumarin TFA; L-Alanine-7-amido-4-methylcoumarin TFA; L-Alanine-7-amido-4-trifluoro-methylcoumarin TFA; L-Alanyl-L-alanyl-L-phenylalanine-7-amido-4-methylcoumarin; L-Alanyl-L-alanyl-L-phenylalanine-7-amido-4-methylcoumarin TFA; D-Alanyl-L-leucyl-L-lysine-7-amido-4-methylcoumarin Salt; L-Arginine-7-amido-4-methylcoumarin hydrochloride; L-Arginyl-L-arginine-7-amido-4-methylcoumarin trihydrochloride; L-Asparagine-7-amido-4-methylcoumarin TFA; L-Aspartic acid-β-(7-amido-4-methylcoumarin); N-α-Benzoyl-DL-arginine-7-amido-4-methylcoumarin; N-α-Benzoyl-L-arginine-7-amido-4-methylcoumarin; N-Benzoyl-L-phenylalanyl-L-valyl-L-arginine-7-amido-4-methylcoumarin; S-Benzyl-L-cysteine-7-amido-4-methylcoumarin; N-BOC-L-phenylalanyl-L-seryl-L-arginine-7-amido-4-methylcoumarin acetate; N-BOC-L-vanyl-glycyl-L-arginine-7-amido-4-methylcoumarin hydrochloride; N-BOC-L-vanyl-L-leucyl-L-lysine-7-amido-4-methylcoumarin Salt; N-α-CBZ-L-arginine-7-amido-4-methylcoumarin hydrochloride; N-CBZ-glycylglycyl-L-leucine-7-amido-4-methylcoumarin; N-CBZ-glycyl-L-proline-7-amido-4-methylcoumarin; N-CBZ-glycyl-L-prolyl-L-arginine-7-amido-4-methylcoumarin; N-β-CBZ-L-lysine-7-amido-4-methylcoumarin; N-CBZ-L-phenylalanyl-L-arginine-7-amido-4-methylcoumarin hydrochloride; N-CBZ-L-prolyl-L-arginine-7-amido-4-methylcoumarin hydrochloride; L-Citrulline-7-amido-4-methylcoumarin hydrochloride; L-Citrulline-7-amido-4-methylcoumarin hydrochloride TFA; D-Glutamic acid-γ-(7-amido-4-methylcoumarin); L-Glutamic acid-α-(7-amido-4-methylcoumarin); L-Glutamine-7-amido-4-methylcoumarin hydrochloride; Glutaryl-glycyl-L-arginine-7-amido-4-methylcoumarin hydrochloride; Glutaryl-glycylglycyl-L-phenylalanine-7-amido-4-methylcoumarin; Glutaryl-L-phenylalanine-7-amido-4-methylcoumarin; Glycine-7-amido-4-methylcoumarin hydrochloride; Glycyl-L-alanine-7-amido-4-methylcoumarin hydrochloride; Glycyl-L-arginine-7-amido-4-methylcoumarin Salt; Glycylglycine-7-amido-4-methylcoumarin hydrochloride; Glycyl-L-phenylalanine-7-amido-4-methylcoumarin; Glycyl-L-proline-7-amido-4-methylcoumarin hydrochloride; L-Histidine-7-amido-4-methylcoumarin; L-Isoleucine-7-amido-4-methylcoumarin; L-Isoleucine-7-amido-4-methylcoumarin TFA; L-Leucine-7-amido-4-methylcoumarin; L-Leucine-7-amido-4-methylcoumarin hydrochloride; L-Leucyl-1-valvyl-1-tyrosine-7-amido-4-methylcoumarin; L-Lysine-7-amido-4-methylcoumarin acetate; L-Methionine-7-amido-4-methylcoumarin acetate; L-Ornithine-7-amido-4-methylcoumarin carbonate; L-Phenylalanine-7-amido-4-methylcoumarin TFA; L-Proline-7-amido-4-methylcoumarin hydrochloride; L-Prolyl-L-phenylalanyl-L-arginine-7-amido-4-methylcoumarin Salt; L-Pyroglutamic acid-7-amido-4-methylcoumarin; L-Serine-7-amido-4-methylcoumarin hydrochloride; L-Seryl-L-tyrosine-7-amido-4-methylcoumarin hydrate; or, L-Tyrosine-7-amido-4-methylcoumarin.

9. The composition of claim 1 wherein said substrate comprises a nutrient moiety, and the nutrient moiety is linked to the signal moiety by a covalent bond.

10. The composition of claim 9 wherein the covalent bond is a peptide bond.

11. The composition of claim 1, wherein the composition comprises two or more substrates for the aminopeptidase, each substrate comprising a signal moiety that causes or produces a substantially identical detectable signal.

12. The composition of claim 1, wherein said detectable moiety is a fluorescent moiety, and said fluorescent moiety is capable of providing a fluorescent signal.

13. The composition of claim 1, wherein said detectable moiety is a chromogen moiety, and said chromogen moiety is capable of providing a signal in the visible, ultraviolet or infrared spectrum.

14. The composition of claim 1 is gel.

15. The composition of claim 1 is liquid.

16. The composition of claim 1 comprised in a powder form.

17. The yeast and/or mold growth medium comprising the composition of claim 1.

18. A method of detecting the presence or amount of yeasts or molds in a test sample, comprising the step of:

inoculating a medium comprising the composition of claim 1 with said test sample;

incubating the inoculated medium under conditions which support the growth of yeasts or molds; and, observing any detectable signal, whereby the presence of a detectable signal indicates the presence of yeasts or molds in the test sample.

19. The method of claim 18 wherein the medium is added to aliquots of serial dilutions of the test sample.

20. The method of claim 19 wherein the medium is added to aliquots of $10^0$, $10^{-1}$, and $10^{-2}$ dilutions of the test sample.

21. The method of claim 16 conducted at a temperature whereby yeasts and molds will grow.

22. The method of claim 21 conducted at a temperature in a temperature range of 20° C. to 35° C.

* * * * *